United States Patent
S. et al.

(10) Patent No.: US 11,367,183 B2
(45) Date of Patent: Jun. 21, 2022

(54) SYSTEMS AND METHODS OF AUTOMATIC FIELD-OF-VIEW (FOV) PRESCRIPTION

(71) Applicant: GE Precision Healthcare, LLC, Milwaukee, WI (US)

(72) Inventors: Deepthi S., Palakkad (IN); Jignesh Dholakia, Bangalore (IN); Dheeraj Kulkarni, Bangalore (IN); Rakesh Shrikant Shevde, Bangalore (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 0 days.

(21) Appl. No.: 16/804,761

(22) Filed: Feb. 28, 2020

(65) Prior Publication Data

US 2021/0272275 A1   Sep. 2, 2021

(51) Int. Cl.
| | |
|---|---|
| *G06K 9/00* | (2022.01) |
| *G06T 7/00* | (2017.01) |
| *G06T 7/194* | (2017.01) |
| *G06K 9/62* | (2022.01) |
| *G06T 7/11* | (2017.01) |
| *G06N 3/08* | (2006.01) |
| *G16H 30/40* | (2018.01) |

(52) U.S. Cl.
CPC .......... *G06T 7/0012* (2013.01); *G06K 9/6256* (2013.01); *G06K 9/6262* (2013.01); *G06N 3/08* (2013.01); *G06T 7/11* (2017.01); *G06T 7/194* (2017.01); *G16H 30/40* (2018.01); *G06T 2207/10088* (2013.01); *G06T 2207/20081* (2013.01); *G06T 2207/20084* (2013.01); *G06T 2207/30016* (2013.01); *G06V 2201/03* (2022.01)

(58) Field of Classification Search
CPC ......... G06T 7/0012; G06T 7/194; G06T 7/11; G06T 2207/10088; G06T 2207/20081; G06T 2207/20084; G06T 2207/30016; G16H 30/40; G06K 9/6256; G06K 9/6262; G06K 2209/05; G06N 3/08
See application file for complete search history.

(56) References Cited

U.S. PATENT DOCUMENTS 8,358,822 B2    1/2013  Sun et al.
2009/0290776 A1*  11/2009  Sun ........................ A61B 5/055
                                          382/131

(Continued)

OTHER PUBLICATIONS

Ronneberger et al., "U-Net: Convolutional Networks for Biomedical Image Segmentation," May 8, 2015, 8 pages.

(Continued)

*Primary Examiner* — Xin Jia
(74) *Attorney, Agent, or Firm* — Armstrong Teasdale LLP (57) ABSTRACT

An automatic field-of-view (FOV) prescription system is provided. The system includes an FOV prescription computing device that includes at least one processor electrically coupled to at least one memory device. The at least one processor is programmed to receive localizer images that depict an anatomy, and generate masks associated with the localizer images, wherein the masks represent part of the localizer images that depict the anatomy. The at least one processor is also programmed to calculate bounding boxes surrounding the anatomy based on the masks, generate an FOV based on the bounding boxes, and output the FOV.

16 Claims, 9 Drawing Sheets

(56) References Cited

U.S. PATENT DOCUMENTS

2011/0228998 A1* 9/2011 Vaidya ................ G01R 33/543
382/131
2020/0037962 A1* 2/2020 Shanbhag .............. A61B 5/055

OTHER PUBLICATIONS

Hu et al., "Variable Field of View for Spatial Resolution Improvement in Continuously Moving Table Magnetic Resonance Imaging," 2005, pp. 146-151.

* cited by examiner

SYSTEMS AND METHODS OF AUTOMATIC FIELD-OF-VIEW (FOV) PRESCRIPTION

BACKGROUND

The field of the disclosure relates generally to systems and methods of prescribing a field of view (FOV), and more particularly, to systems and methods of automatically prescribing an FOV for acquisition of medical images.

An FOV includes a location and dimensions of anatomy in a patient, for which medical images will be acquired. In acquiring medical images using an imaging modality such as a magnetic resonance imaging (MRI) system, an FOV needs to be prescribed in order for the MRI system to acquire medical images of the anatomy within the FOV. In conventional systems, localizer images are acquired, and then a technologist manually prescribes an FOV based on the localizer images. The accuracy and consistency of the prescribed FOV depends on the skill level of the technologist. A sub-optimal FOV may lead to increased scan time and artifacts in the acquired images.

BRIEF DESCRIPTION

In one aspect, an automatic field-of-view (FOV) prescription system is provided. The system includes an FOV prescription computing device. The FOV prescription computing device includes at least one processor electrically coupled to at least one memory device. The at least one processor is programmed to receive localizer images that depict an anatomy, and generate masks associated with the localizer images, wherein the masks represent part of the localizer images that depict the anatomy. The at least one processor is also programmed to calculate bounding boxes surrounding the anatomy based on the masks, generate an FOV based on the bounding boxes, and output the FOV.

In another aspect, a computer-implemented method of automatically prescribing an FOV is provided. The method includes receiving localizer images that depict an anatomy, and generating masks associated with the localizer images, wherein the masks represent part of the localizer images that depict the anatomy. The method also includes calculating bounding boxes surrounding the anatomy based on the masks, generating an FOV based on the bounding boxes, and outputting the FOV.

In yet another aspect, an automatic FOV prescription system is provided. The system includes an FOV prescription computing device. The FOV prescription computing device includes at least one processor electrically coupled to at least one memory device. The at least one processor is programmed to execute a neural network model for analyzing images, and receive training images depicting anatomies and observed masks associated with the training images, wherein the observed masks are masks for the training images such that anatomies depicted by the training images are inside the observed masks. The at least one processor is also programmed to analyze the training images, generate predicted masks for the training images using the neural network model, and compare the predicted masks with the observed masks. Further, the at least one processor is programmed to adjust the neural network model based on the comparison.

DETAILED DESCRIPTION

The disclosure includes systems and methods of automatically prescribing a field of view (FOV) in an imaging modality. In the systems and methods described herein, an FOV is automatically prescribed based on masks that are associated with localizer images and generated using a neural network model. For the purpose of detailed description, the imaging modality of magnetic resonance (MR) systems and MR images are used herein as examples only. The systems and methods described herein, however, are not limited to MR systems or MR images, and may be applied to other imaging modalities, such as computed tomography (CT) and positron emission tomography (PET).

In magnetic resonance imaging (MRI), a subject is placed in a magnet. A subject is a human (live or deceased), an animal (live or deceased), or part of a human or an animal. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

Figure 1:
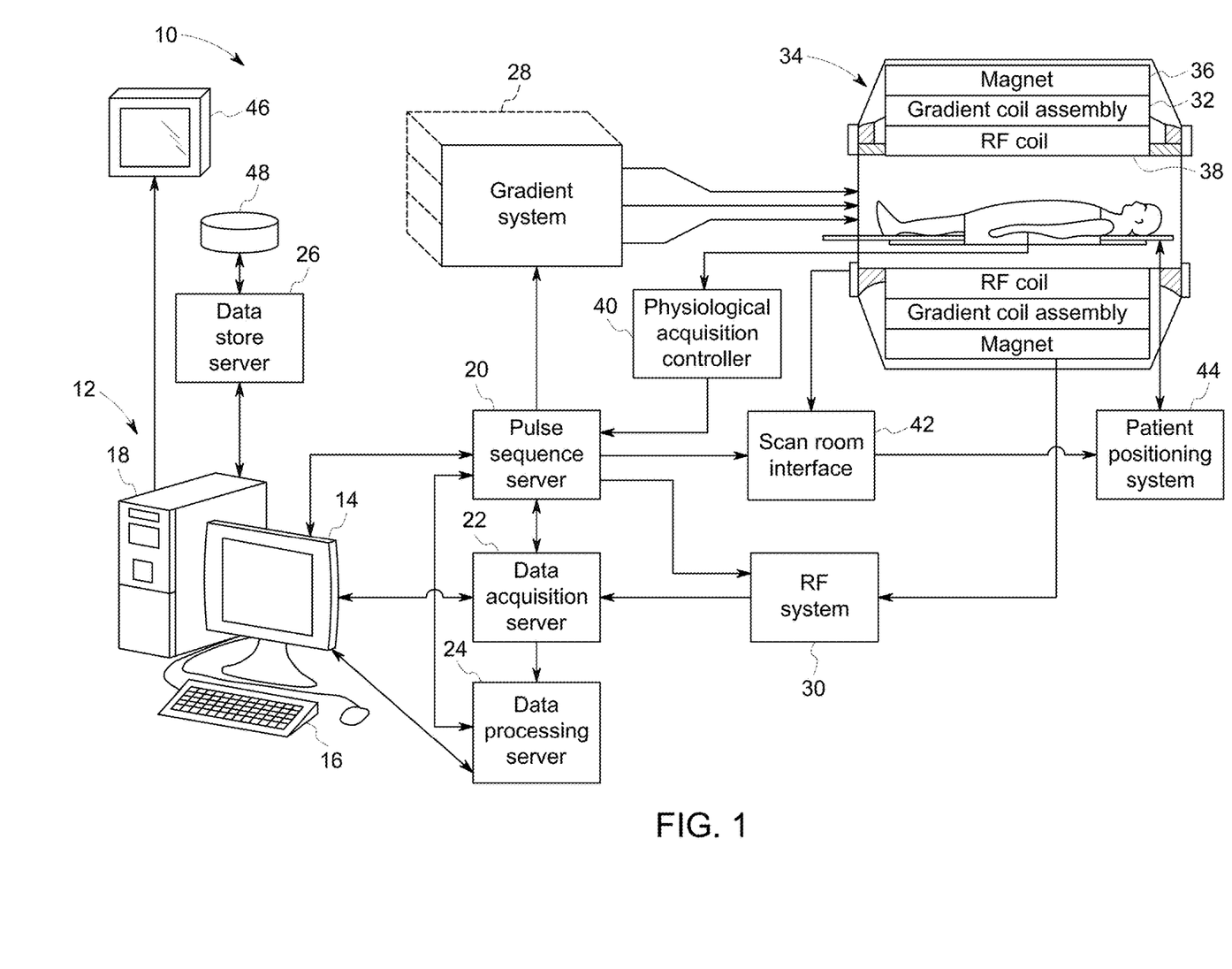
FIG. 1 is a schematic diagram of an exemplary magnetic resonance imaging (MRI) system.

FIG. 1 illustrates a schematic diagram of an exemplary MRI system 10. In the exemplary embodiment, the MRI system 10 includes a workstation 12 having a display 14 and a keyboard 16. The workstation 12 includes a processor 18, such as a commercially available programmable machine running a commercially available operating system. The workstation 12 provides an operator interface that allows scan prescriptions to be entered into the MRI system 10. The workstation 12 is coupled to a pulse sequence server 20, a data acquisition server 22, a data processing server 24, and a data store server 26. The workstation 12 and each server 20, 22, 24, and 26 communicate with each other.

In the exemplary embodiment, the pulse sequence server 20 responds to instructions downloaded from the workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. The RF coil 38 is shown as a whole body RF coil. The RF coil 38 may also be a local coil that may be placed in proximity to the anatomy to be imaged, or a coil array that includes a plurality of coils.

In the exemplary embodiment, gradient waveforms used to perform the prescribed scan are produced and applied to the gradient system 28, which excites gradient coils in the gradient coil assembly 32 to produce the magnetic field gradients $G_x$, $G_y$, and $G_z$ used for position-encoding MR signals. The gradient coil assembly 32 forms part of a magnet assembly 34 that also includes a polarizing magnet 36 and the RF coil 38.

In the exemplary embodiment, the RF system 30 includes an RF transmitter for producing RF pulses used in MR pulse sequences. The RF transmitter is responsive to the scan prescription and direction from the pulse sequence server 20 to produce RF pulses of a desired frequency, phase, and pulse amplitude waveform. The generated RF pulses may be applied to the RF coil 38 by the RF system 30. Responsive MR signals detected by the RF coil 38 are received by the RF system 30, amplified, demodulated, filtered, and digitized under direction of commands produced by the pulse sequence server 20. The RF coil 38 is described as a transmitter and receiver coil such that the RF coil 38 transmits RF pulses and detects MR signals. In one embodiment, the MRI system 10 may include a transmitter RF coil that transmits RF pulses and a separate receiver coil that detects MR signals. A transmission channel of the RF system 30 may be connected to a RF transmission coil and a receiver channel may be connected to a separate RF receiver coil. Often, the transmission channel is connected to the whole body RF coil 38 and each receiver section is connected to a separate local RF coil.

In the exemplary embodiment, the RF system 30 also includes one or more RF receiver channels. Each RF receiver channel includes an RF amplifier that amplifies the MR signal received by the RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M=\sqrt{I^2+Q^2} \quad (1);$$

and the phase of the received MR signal may also be determined as in Eq. (2) below:

$$\varphi = \tan^{-1}\left(\frac{Q}{I}\right). \quad (2)$$

In some embodiments, the pulse sequence server 20 also optionally receives subject data from a physiological acquisition controller 40. The controller 40 receives physiological signals from sensors connected to the subject, such as electrocardiograph ("ECG") signals from electrodes, or respiratory signals from a respiratory monitoring device such as a bellows. The physiological signals are typically used by the pulse sequence server 20 to synchronize, or "gate," the performance of the scan with the subject's heart beat or respiration.

In the exemplary embodiment, the pulse sequence server 20 also connects to a scan room interface circuit 42 that receives signals from sensors associated with the condition of the subject and the magnet system. Through the scan room interface circuit 42, a patient positioning system 44 receives commands to move the subject to desired positions before and/or during the scan.

In the exemplary embodiment, the digitized MR signal samples produced by the RF system 30 are received by the data acquisition server 22. The data acquisition server 22 may operate in response to instructions downloaded from the workstation 12 to receive real-time MR data and provide buffer storage such that no data is lost by data overrun. In some scans, the data acquisition server 22 does little more than pass the acquired MR data to the data processing server 24. In scans that need information derived from acquired MR data to control further performance of the scan, however, the data acquisition server 22 is programmed to produce the needed information and convey it to the pulse sequence server 20. For example, during prescans, MR data is acquired and used to calibrate the pulse sequence performed by the pulse sequence server 20. Also, navigator signals may be acquired during a scan and used to adjust the operating parameters of the RF system 30 or the gradient system 28, or to control the view order in which k-space is sampled.

In the exemplary embodiment, the data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the exemplary embodiment, images reconstructed by the data processing server 24 are conveyed back to the workstation 12 where they are stored. In some embodiments, real-time images are stored in a database memory cache (not shown in FIG. 1), from which they may be output to operator display 14 or a display 46 that is located near the magnet assembly 34 for use by attending physicians. Batch mode images or selected real time images may be stored in a host database on disc storage 48 or on a cloud. When such images have been reconstructed and transferred to storage, the data processing server 24 notifies the data store server 26 on the workstation 12. The workstation 12 may be used by an operator to archive the images, produce films, or send the images via a network to other facilities.

Figure 2:
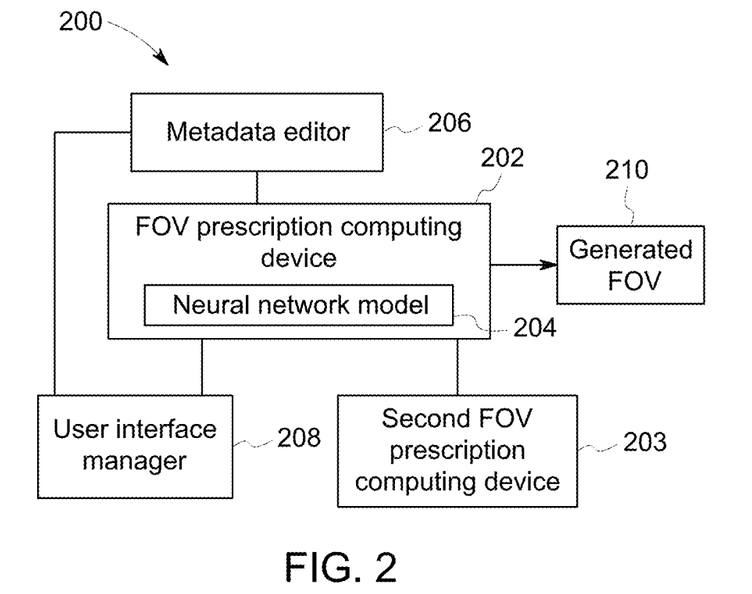
FIG. 2 is an exemplary field-of-view (FOV) prescription system.

FIG. 2 is a schematic diagram of an exemplary system 200 for automatic FOV prescription. An FOV is an area or volume in a subject that is to be imaged, and may include dimensions in the x, y, z directions. In an MRI system, x refers to frequency-encoding direction, y refers to phase-encoding direction, and z refers to a slice-selection direction or a second phase-encoding direction for a three-dimensional (3D) acquisition. In the exemplary embodiment, the system 200 includes an FOV prescription computing device 202 configured to automatically prescribe an FOV. The FOV prescription computing device 202 further includes a neural network model 204. The system 200 may include a second FOV prescription computing device 203. The second FOV prescription computing device 203 may be used to train neural network model 204, and the FOV prescription computing device 202 may then use the trained neural network model 204. The second FOV prescription computing device 203 may be the same computing device as the FOV prescription computing device 202 such that the training and use of the neural network model 204 are done on one computing device. Alternatively, the second FOV prescription computing device 203 may be a separate computing device from the FOV prescription computing device 202 such that the training and use of the neural network model 204 are done on separate computing devices.

The FOV prescription computing device 202 is configured to automatically generate an FOV 210 based on one or more localizer images and output the generated FOV 210. The FOV prescription computing device 202 may be implemented in the workstation 12 of the MRI system 10, or may be implemented on a separate computing device that is communicated with the workstation 12. Instructions of the pulse sequence for acquiring one or more images having the generated FOV are generated based on the generated FOV and are sent to the pulse sequence server 20 to further operate the RF coil 38 and the gradient coil assembly 32.

In the exemplary embodiment, the system 200 further includes a metadata editor 206 configured to update the metadata of the images. The system 200 may further include a user interface manager 208 configured to receive user inputs on choices in prescribing an FOV.

FIGS. 3A-4F show an FOV is generated based on localizer images 301, 402a-402e that depict an anatomy 303 of a human brain. In medical imaging, images may be displayed as a series of axial, sagittal, and/or coronal images. Localizer images 301, 402a-402e are axial images of a human brain. Localizer images are acquired through localizer scans that may include a set of three-plane, low resolution, large FOV scans acquiring images depicting a part of body in the subject, such as head, chest, abdomen, or extremities. The localizer images are used to locate the anatomy of interest in the part of body, such as a heart in the chest. The localizer images will be used for plotting FOV and slices in the later scans of the subject that have a relatively higher resolution and a smaller FOV than the localizer scans or may be used to acquire dynamic or functional images of the anatomy.

Figure 3A:
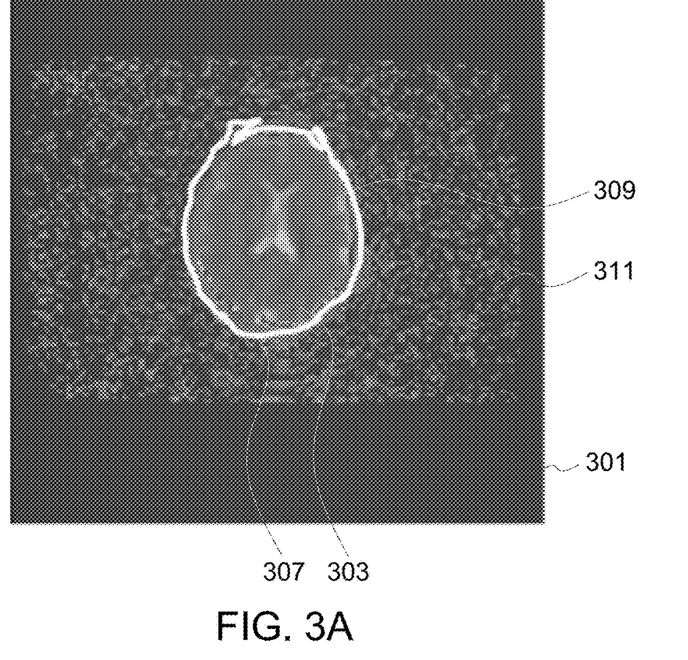
FIG. 3A is an exemplary MRI localizer image.
Figure 3B:
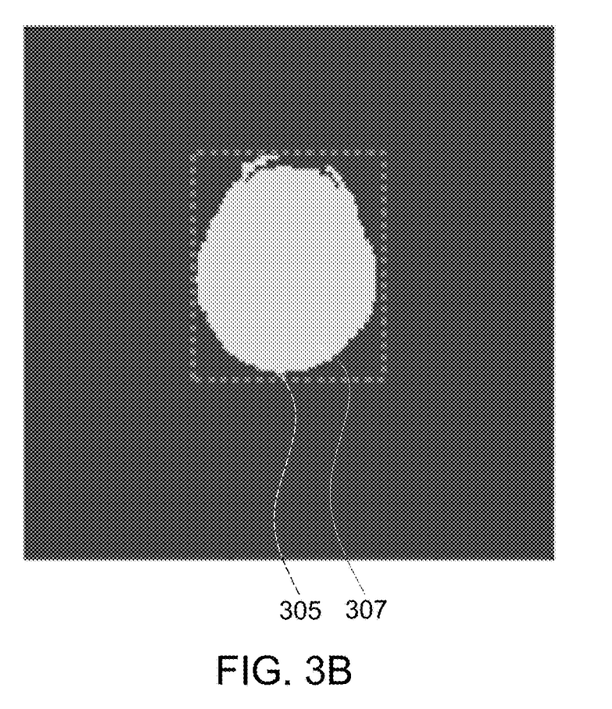
FIG. 3B is an illustration of a mask based on the localizer image shown in FIG. 3A.

FIG. 3B shows a bounding box 305 is generated based on the localizer image 301 (shown in FIG. 3A). In the exemplary embodiment, a mask 307 associated with the localizer image 301 is generated. The mask 307 may be generated using the neural network model 204. The mask 307 represents part of the localizer image 301 that depicts the anatomy 303. That is, in the localizer image 301, the anatomy 303 is inside the mask 307 (see FIG. 3A). The neural network model 204 is configured to generate the mask corresponding to the localizer image 301. The neural network model 204 may be trained with training localizer images as inputs and observed masks corresponding to the training localizer images as outputs. The network model 204 may be adjusted during the training based on the comparison of masks for the training localizer images predicted by the neural network model 204 and the observed masks.

In the exemplary embodiment, a bounding box 305 is then generated based on the mask 307. In some embodiment, the bounding box 305 is a rectangle that surrounds mask 307. The bounding box 305 is oriented in the same direction as the localizer image 301.

In some embodiments, the localizer image 301 is segmented into a foreground 309 and a background 311 based on the mask 307 (as shown in FIG. 3A). The foreground 309 includes the part of the localizer image 301 that is inside the mask 307 and depicts the anatomy 303. The background 311 includes the part of the localizer image 301 that is outside the mask 307 and does not depict the anatomy 303. The foreground 309 and the background 311 may be saved for use in processing images. For example, the background 311 may be used to selectively reduce noise in an MR image by applying an intensity threshold to the background 311 but not to the foreground 309, which allows increased background noise reduction while reducing or eliminating holes in anatomical regions of medical images.

Figure 4A:
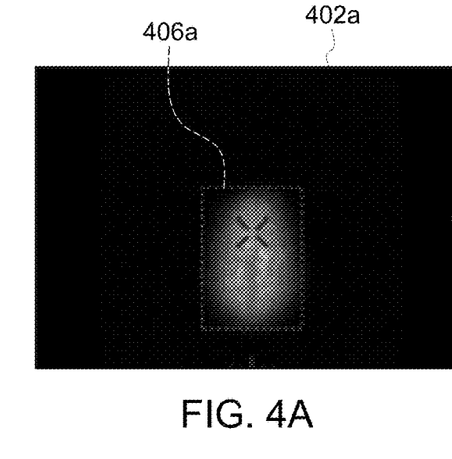
FIGS. 4A-4E are exemplary MRI localizer images acquired by a localizer scan.
Figure 4B:
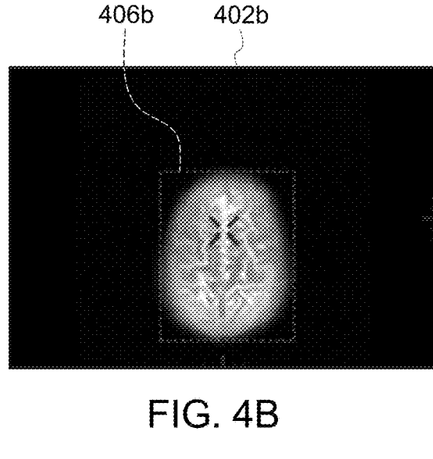
Figure 4C:
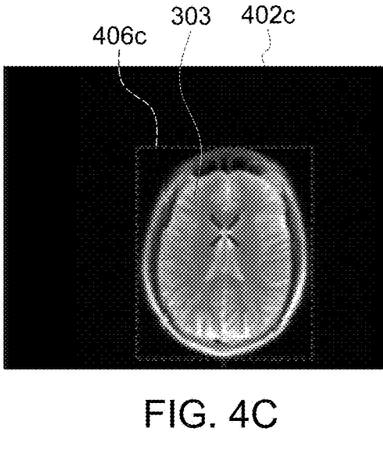
Figure 4D:
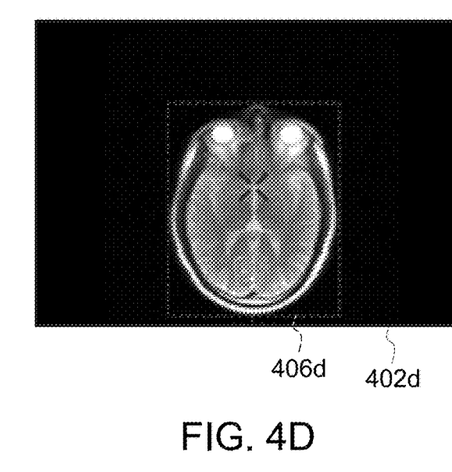
Figure 4E:
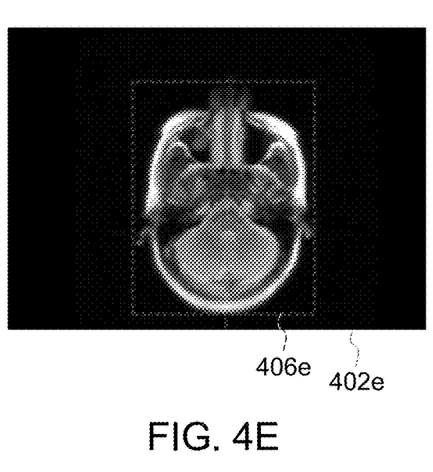
Figure 4F:
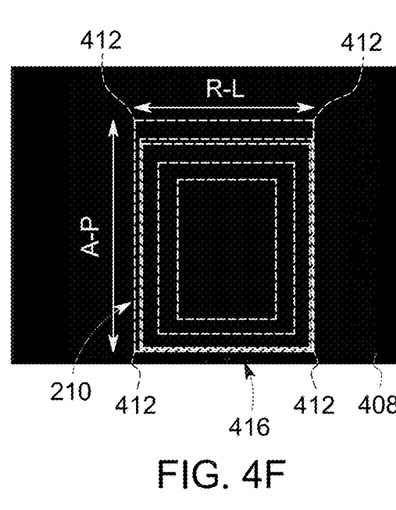
FIG. 4F is an illustration of an FOV generated using the bounding boxes for the localizer images shown in FIGS. 4A-4E.

FIGS. 4A-4F show an FOV generated based on bounding boxes 406a-406e corresponding to localizer images 402a-402e. Localizer images 402a-402e are axial images of the anatomy 303 starting from the superior of the subject in the image 402a to the inferior of the subject in the image 402e. In the exemplary embodiment, bounding boxes 406a-406e associated with localizer images 402a-402e are generated, similar to the generation of the bounding box 305. The bounding boxes 406a-406e surround the anatomy 303. To derive an FOV 210 in the right-left (R-L) and anterior-posterior (A-P) directions, a union of the bounding boxes 406a-406e are projected onto a reference frame 408 to derive projected bounding boxes 416 (as shown in FIG. 4F). The Reference frame 408 has the same orientation as localizer images 402a-402e. As such, the projected bounding boxes 416 have the same size and location as their corresponding bounding boxes 406a-406e. The corner points 412 of the union of the projected bounding boxes 416 are used as basis for the FOV 210 in the R-L and A-P directions such that the FOV 210 fully covers anatomy 303. The in-plane center of FOV 210 may be chosen as the center of the union of projected bounding boxes 416. To derive the FOV 210 in the superior-inferior (S-I) direction, sagittal localizer images (not shown) may be used. Similarly, the FOV 210 in the S-I and A-P directions are calculated based on the corner points of the union of projected bounding boxes for the sagittal localizer images, where the union of projected bounding boxes are derived by projecting the bounding boxes of the sagittal localizer images onto a reference frame having the same orientation as the sagittal localizer images. In some embodiments, a dimension of the FOV 210 may be increased, for example by 5%, in at least one of the directions to compensate for segmentation inaccuracy. For example, the dimension of the FOV 210 in the R-L direction, the A-P direction, or both, is increased by 5%. The amount of increase may vary, and may be modified by a user through the user interface manager 208. The in-plane center of FOV 210 is accordingly adjusted to account for the increase.

Figure 5A:
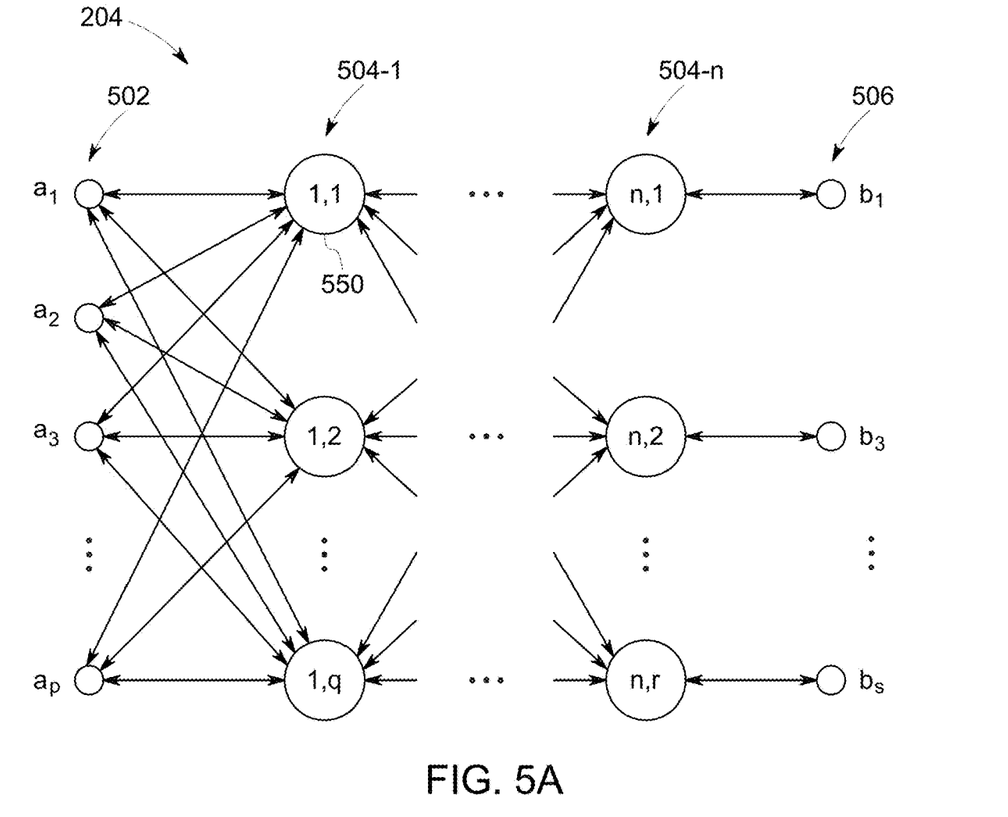
FIG. 5A is a schematic diagram of a neural network.

FIG. 5A depicts an exemplary artificial neural network model 204. The exemplary neural network model 204 includes layers of neurons 502, 504-1 to 504-$n$, and 506, including an input layer 502, one or more hidden layers 504-1 through 504-$n$, and an output layer 506. Each layer may include any number of neurons, i.e., q, r, and n in FIG. 5A may be any positive integers. It should be understood that neural networks of a different structure and configuration from that depicted in FIG. 5A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 204 changes during the training process, and some neurons are bypassed or ignored if, for example, during execution of the neural network, they are determined to be of less relevance.

In the exemplary embodiment, each neuron in hidden layer(s) 504-1 through 504-$n$ processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 204 are obtained from a hidden layer 504-1 through 504-$n$ in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-$n$ may share decisions relating to labeling, with no single layer making an independent decision as to labeling.

Figure 5B:
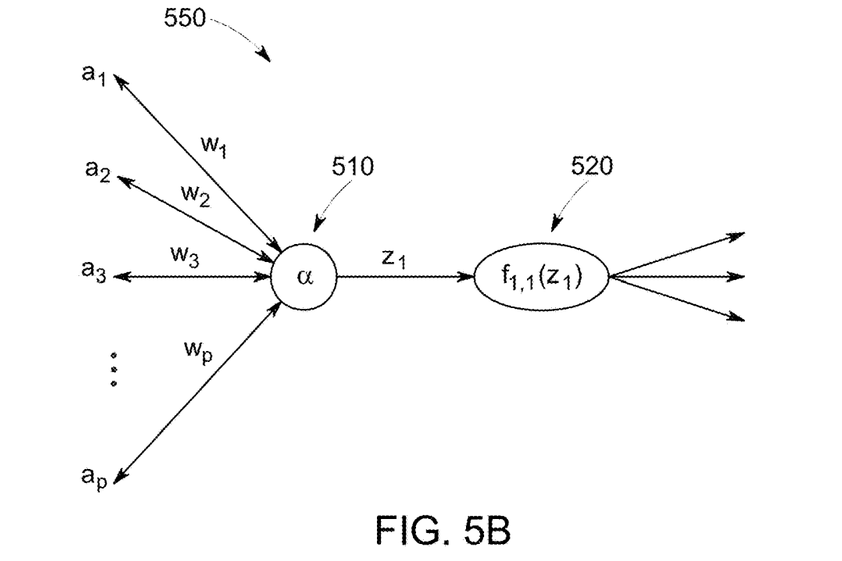
FIG. 5B is a schematic diagram of a neuron in the neural network shown in FIG. 5A.

FIG. 5B depicts an example neuron 550 that corresponds to the neuron labeled as "1,1" in hidden layer 504-1 of FIG. 5A, according to one embodiment. Each of the inputs to the neuron 550 (e.g., the inputs in the input layer 502 in FIG. 5A) is weighted such that input $a_1$ through $a_p$ corresponds to weights $w_1$ through $w_p$ as determined during the training process of the neural network model 204.

In some embodiments, some inputs lack an explicit weight, or have a weight below a threshold. The weights are applied to a function a (labeled by a reference numeral 510), which may be a summation and may produce a value $z_1$ which is input to a function 520, labeled as $f_{1,1}(z_1)$. The function 520 is any suitable linear or non-linear function. As depicted in FIG. 5B, the function 520 produces multiple outputs, which may be provided to neuron(s) of a subsequent layer, or used as an output of the neural network model 204. For example, the outputs may correspond to index values of a list of labels, or may be calculated values used as inputs to subsequent functions.

It should be appreciated that the structure and function of the neural network model 204 and the neuron 550 depicted are for illustration purposes only, and that other suitable configurations exist. For example, the output of any given neuron may depend not only on values determined by past neurons, but also on future neurons.

The neural network model 204 may include a convolutional neural network (CNN), a deep learning neural network, a reinforced or reinforcement learning module or program, or a combined learning module or program that learns in two or more fields or areas of interest. The neural network model 204 may be trained using supervised or unsupervised machine learning programs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, and object statistics and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

Based upon these analyses, the neural network model 204 may learn how to identify characteristics and patterns that may then be applied to analyzing image data, model data, and/or other data. For example, the model 204 may learn to identify a mask of an input image.

Figure 6:
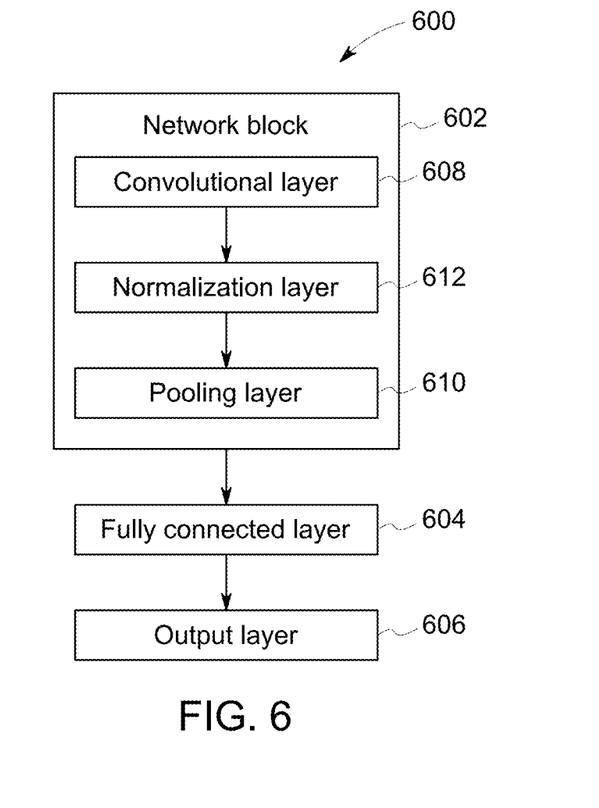
FIG. 6 is a block diagram of an exemplary convolutional neural network.

FIG. 6 is a schematic diagram of an exemplary CNN 600 that may be included in the neural network model 204. The CNN 600 includes a convolutional layer 608. In a convolutional layer, convolution is used in place of general matrix multiplication in a neural network model. In one example, a 1×1 convolution is used to reduce the number of channels in the neural network 600. The neural network 600 includes one or more convolutional layer blocks 602, a fully-connected layer 604 where the neurons in this layer is connected with every neuron in the prior layer, and an output layer 606 that provides outputs.

In the exemplary embodiment, the convolutional layer block 602 includes a convolutional layer 608 and a pooling layer 610. Each convolutional layer 608 is flexible in terms of its depth such as the number of convolutional filters and sizes of convolutional filters. The pooling layer 610 is used to streamline the underlying computation and reduce the dimensions of the data by combining outputs of neuron clusters at the prior layer into a single neuron in the pooling layer 610. The convolutional layer block 602 may further include a normalization layer 612 between the convolutional layer 608 and the pooling layer 610. The normalization layer 612 is used to normalize the distribution within a batch of training images and update the weights in the layer after the normalization. The number of convolutional layer blocks 602 in the neural network 600 may depend on the image quality of training images, and levels of details in extracted features.

In operation, in training, training images and other data such as extracted features of the training images are inputted into one or more convolutional layer blocks 602. Observed masks corresponding to the training images are provided as outputs of the output layer 606. Neural network 600 is adjusted during the training. Once the neural network 600 is trained, an input image is provided to the one or more convolutional layer blocks 602 and the output layer 606 provides outputs that include a mask associated with the input image.

Figure 7:
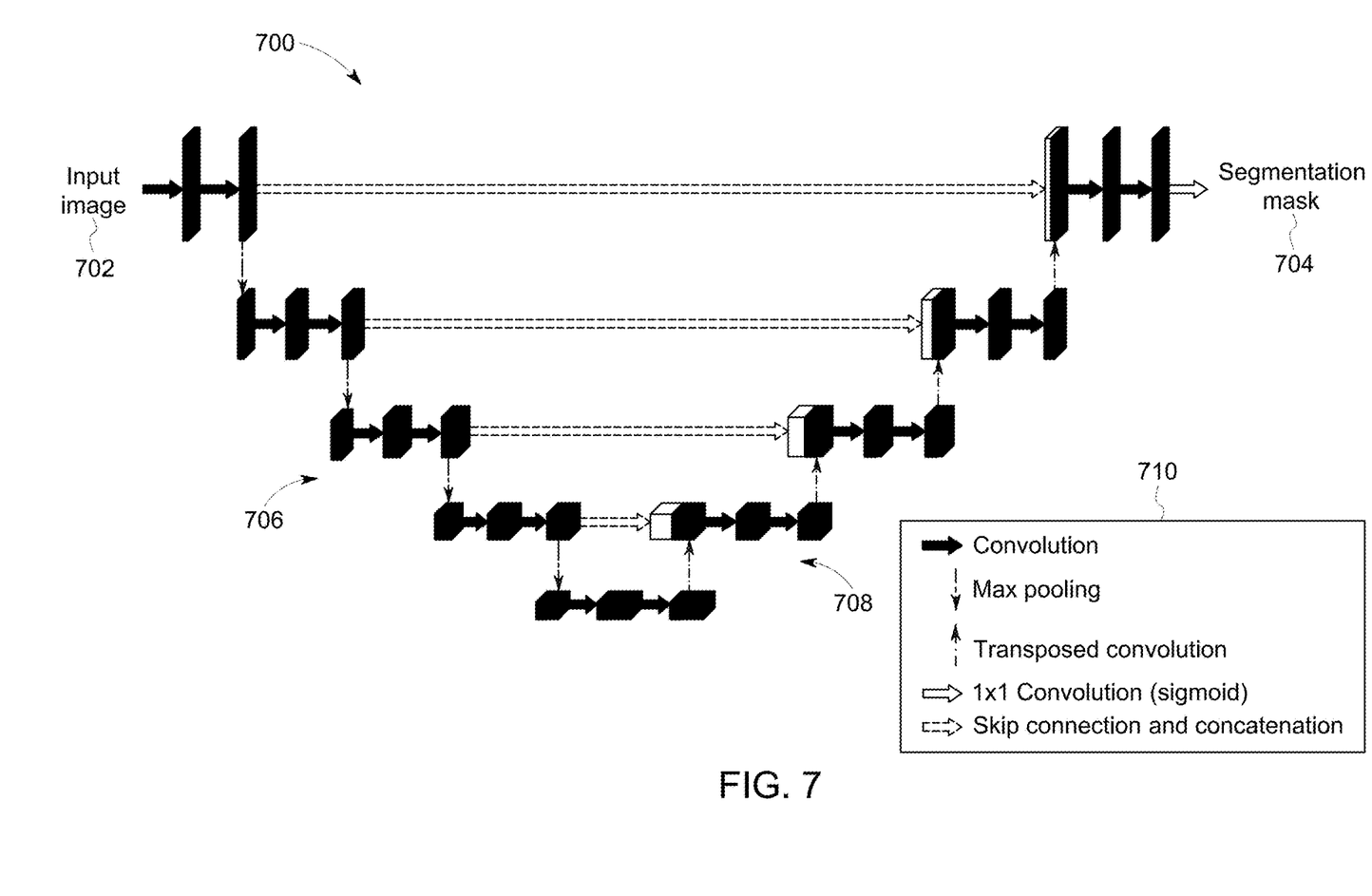
FIG. 7 is a block diagram of an exemplary U-Net.

Turning to FIG. 7, a schematic diagram of an exemplary U-Net 700 is shown. The neural network model 204 may include the U-Net 700. A U-Net is a CNN. The U-Net 700 is configured to take an input image 702 as an input and output a segmentation mask 704. The U-Net 700 includes a contracting path 706 and an expansive pathway 708, which gives the network a u-shaped architecture. The contracting path 706 is a typical convolutional network that includes repeated application of convolutions, each followed by a rectified linear unit and a max pooling operation. During the contraction, the spatial information is reduced while feature information is increased. The expansive pathway 708 combines the feature and spatial information through a sequence of up-convolutions and concatenations with high-resolution features from the contracting path 706.

In the exemplary embodiment, the tiles in the diagram indicate feature maps in U-Net 700. Solid filled tiles correspond to feature maps. Unfilled tiles correspond to copied and cropped feature maps. The transformations/mappings performed by each feature map are indicated by arrows, where each type of arrow corresponds to a unique transformation, as indicated by a legend 710. Solid filled arrows indicate convolutions. Downward pointing arrows indicate max pooling. Upward pointing arrows indicate up convolutions or transposed convolutions, where the spatial resolution of the feature map is increased. Rightward pointing dash-unfilled arrows indicate skipping connection and concatenation, and the feature maps are copied and cropped. Rightward pointing solid-unfilled arrows indicate a 1×1 convolution, in which each feature channel in an immediately preceding feature map is mapped to a single feature channel of a current feature map, or in other words, a 1-to-1 mapping of feature channels between an immediately preceding feature map and a current feature map occurs. Processing at every feature map may include the above-described convolutions as well as activations, where activation mappings are non-linear functions that restrict the output values of the processing to a bounding range.

Figure 8:
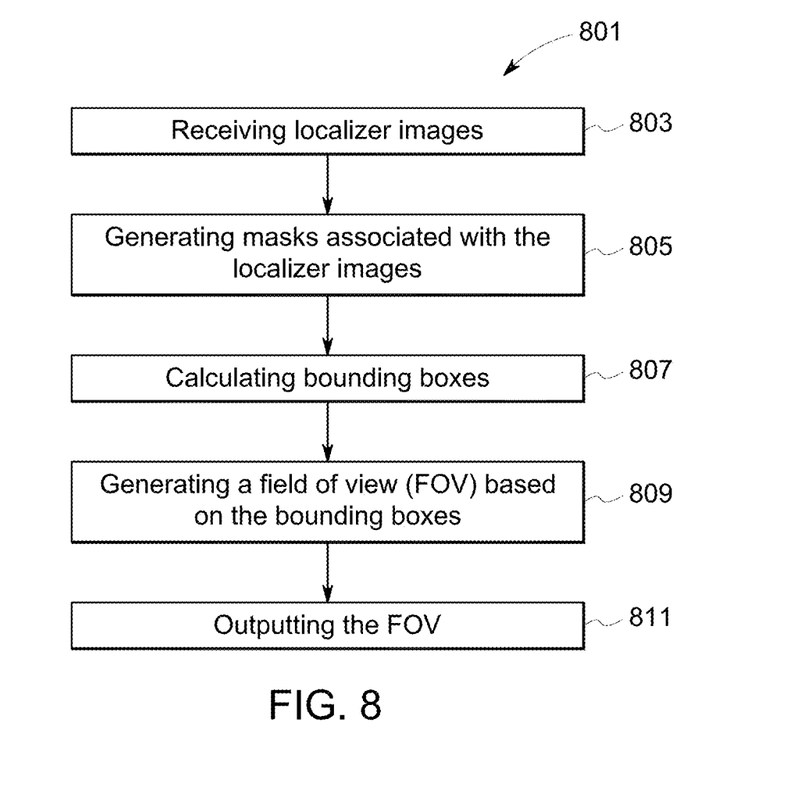
FIG. 8 is a flow chart of an exemplary method of automatically prescribing an FOV.

FIG. 8 is a flow chart of an exemplary method 801 of automatically prescribing an FOV. The method 801 includes receiving 803 localizer images that depict an anatomy of the subject. The method 801 further includes generating 805 masks associated with the localizer images. The masks represent part of the localizer images that depict the anatomy. Further, the method 801 includes calculating 807 bounding boxes surrounding the anatomy based on the masks. Moreover, the method 801 includes generating 809 an FOV based on the bounding boxes. The method 801 also includes outputting 811 the FOV.

Figure 9:
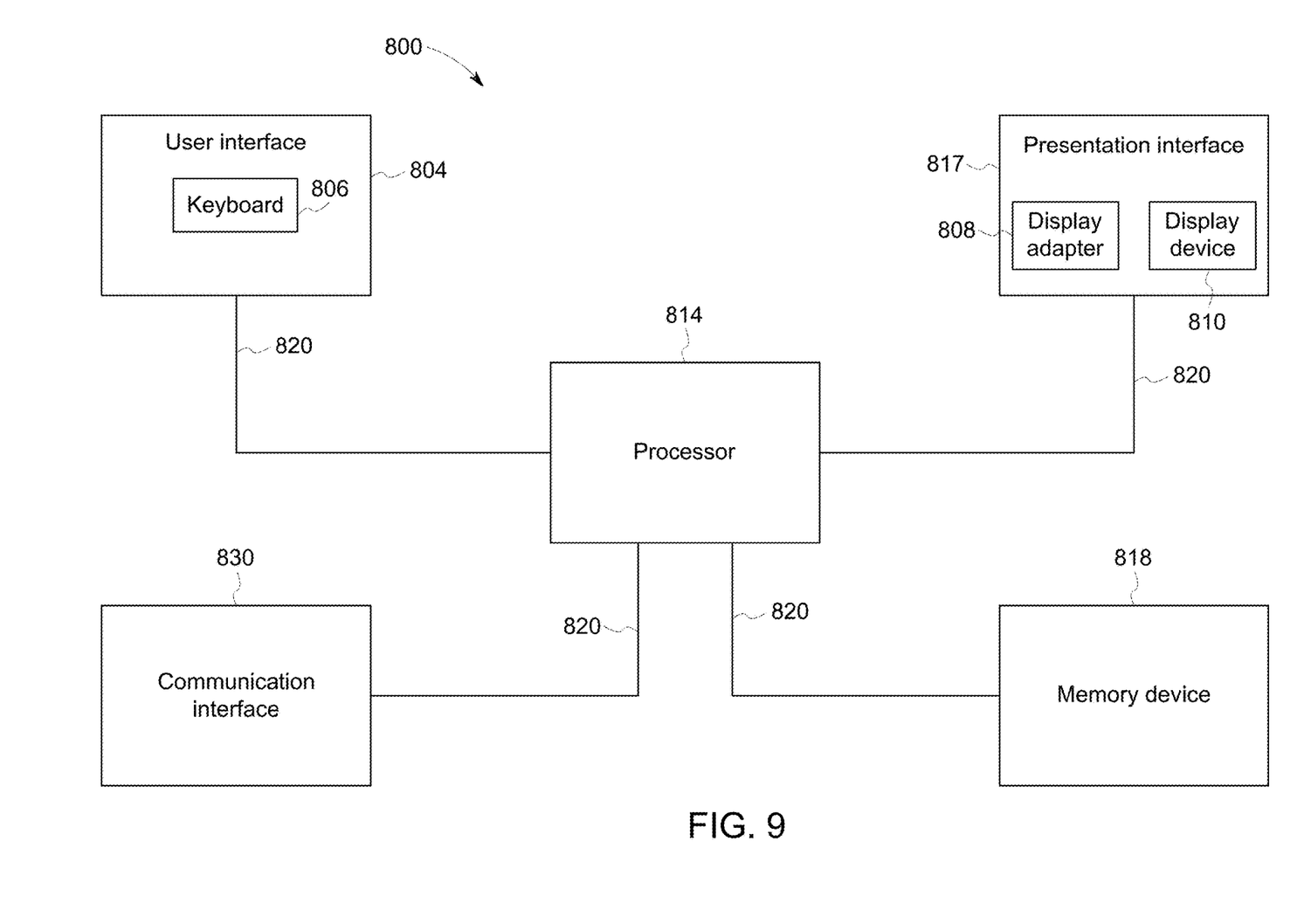
FIG. 9 is a block diagram of an exemplary computing device.

The workstation 12 and the FOV prescription computing device 202, 203 described herein may be implemented on any suitable computing device 800 and software implemented therein. FIG. 9 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) automatic generation of an FOV; (b) elimination of manual prescription of an FOV; and (c) use of a neural network model to identify the anatomy boundary in a medical image.

Exemplary embodiments of systems and methods of automatic prescription of FOVs are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An automatic field-of-view (FOV) prescription system, comprising an FOV prescription computing device, said FOV prescription computing device comprising at least one processor electrically coupled to at least one memory device, and said at least one processor programmed to:
   receive localizer images that depict an anatomy;
   generate masks associated with the localizer images using a neural network model, wherein the masks represent part of the localizer images that depict the anatomy;
   calculate bounding boxes surrounding the anatomy based on the masks;
   generate an FOV based on the bounding boxes by:
   projecting the bounding boxes onto a reference frame having the same orientation as the localizer images to form a union of projected bounding boxes; and
   generating the FOV based on corner points of the union of the projected bounding boxes; and
   output the FOV.

2. The system of claim 1, wherein said at least one processor is further programmed to:
   determine a center of the union of the projected bounding boxes; and
   set the center of the union of the projected bounding boxes as an in-plane center of the FOV.

3. The system of claim 1, wherein said at least one processor is further programmed to:
   increase a dimension of the generated FOV by 5% in at least one direction.

4. The system of claim 1, wherein the neural network model includes a convolutional neural network.

5. The system of claim 4, wherein the neural network model includes a U-Net.

6. The system of claim 1, wherein the neural network model is trained with training localizer images as inputs and masks associated with the training localizer images as outputs.

7. The system of claim 1, wherein said at least one processor is further programmed to:
   execute the neural network model;
   analyze the localizer images using the neural network model; and
   generate the masks associated with the localizer images based on the analysis.

8. The system of claim 1, wherein said at least one processor is further programmed to:
   segment the localizer images into foregrounds and backgrounds using the masks, wherein the foregrounds include part of the localizer images inside the masks and the backgrounds include part of the localizer images outside the masks; and
   output the backgrounds.

9. A computer-implemented method of automatically prescribing a field of view (FOV), said method comprising:
   receiving localizer images that depict an anatomy;
   generating masks associated with the localizer images, wherein the masks represent part of the localizer images that depict the anatomy;
   segmenting the localizer images into foregrounds and backgrounds using the masks, wherein the foregrounds include part of the localizer images inside the masks and the backgrounds include part of the localizer images outside the masks;
   outputting the backgrounds;
   calculating bounding boxes surrounding the anatomy based on the masks;
   generating an FOV based on the bounding boxes; and
   outputting the FOV.

10. The method of claim 9, wherein generating mask further comprises generating the masks using a neural network model.

11. The method of claim 9, further comprising:
    projecting the bounding boxes onto a reference frame having the same orientation as the localizer images to form a union of projected bounding boxes; and
    generating the FOV based on corner points of the union of the projected bounding boxes.

12. The method of claim 11, further comprising:
    determining a center of the union of the projected bounding boxes; and
    setting the center of the union of the projected bounding boxes as an in-plane center of the FOV.

13. The method of claim 9, further comprising:
    increasing a dimension of the generated FOV by 5% in at least one direction.

14. The method of claim 9, further comprising generating the masks using a neural network model, wherein the neural network model includes a U-Net.

15. The method of claim 9, further comprising generating the masks using a neural network model, wherein the neural network model is trained with training localizer images as inputs and masks associated with the training localizer images as outputs.

16. The method of claim 9, further comprising:
    executing a neural network model;
    analyzing the localizer images using the neural network model; and
    generating the masks associated with the localizer images based on the analysis.

* * * * *